US010893805B2

(12) United States Patent
Luther et al.

(10) Patent No.: US 10,893,805 B2
(45) Date of Patent: Jan. 19, 2021

(54) METHOD OF AND APPARATUS FOR CHARACTERIZING SPATIAL-TEMPORAL DYNAMICS OF MEDIA EXCITABLE FOR DEFORMATION

(71) Applicant: Max-Planck-Gesellschaft zur Foerderung der Wissenschaften e.V., Munich (DE)

(72) Inventors: Stefan Luther, Goettingen (DE); Jan Christoph, Goettingen (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 505 days.

(21) Appl. No.: 15/642,735

(22) Filed: Jul. 6, 2017

(65) Prior Publication Data

US 2017/0319068 A1    Nov. 9, 2017

Related U.S. Application Data

(63) Continuation of application No. PCT/EP2015/077001, filed on Nov. 18, 2015.

(30) Foreign Application Priority Data

Jan. 9, 2015    (EP) .................... 15150588

(51) Int. Cl.
*A61B 5/00*    (2006.01)
*G16H 50/50*    (2018.01)
(Continued)

(52) U.S. Cl.
CPC .......... *A61B 5/0044* (2013.01); *A61B 5/0035* (2013.01); *A61B 5/0066* (2013.01);
(Continued)

(58) Field of Classification Search
CPC ..... A61B 5/0044; A61B 8/0883; A61B 8/485; A61B 5/0066; A61B 5/055;
(Continued)

(56) References Cited

U.S. PATENT DOCUMENTS 8,666,138 B2    3/2014 Otani et al.
2004/0267321 A1* 12/2004 Boileau .............. A61B 5/04525
607/3

(Continued)

FOREIGN PATENT DOCUMENTS

| JP | 2009-28362 | 2/2009 |
| WO | 2013/123549 A1 | 8/2013 |
| WO | 2014/059170 A1 | 4/2014 |

OTHER PUBLICATIONS

Provost et al., "Imaging the electromechanical activity of the heart in vivo", PNAS May 24, 2011, vol. 108, No. 21, 8565-8570 (Year: 2011).*

(Continued)

*Primary Examiner* — Bill Thomson
*Assistant Examiner* — Aminah Asghar
(74) *Attorney, Agent, or Firm* — Thomas | Horstemeyer, LLP (57) ABSTRACT

For characterizing spatial-temporal dynamics of a medium (1) excitable for deformation, an elastic model of the medium is defined. The medium is imaged at consecutive points in time to obtain a series of images. Shifts of structures of the medium (1) between the images of the series are determined. A dynamic description of a temporal development of spatial deformations of a predefined elastic model of the medium (1) is adapted to match the shifts of the structures; and temporal developments of rate of deformation patterns in the medium (1) are identified from the dynamic description.

19 Claims, 5 Drawing Sheets

(51) Int. Cl.
*A61B 8/08* (2006.01)
*A61B 5/055* (2006.01)
*A61B 5/04* (2006.01)
*G16H 30/40* (2018.01)

(52) U.S. Cl.
CPC ........ *A61B 5/0071* (2013.01); *A61B 5/04011* (2013.01); *A61B 5/055* (2013.01); *A61B 5/743* (2013.01); *A61B 8/0883* (2013.01); *A61B 8/485* (2013.01); *G16H 30/40* (2018.01); *G16H 50/50* (2018.01); *A61B 2576/023* (2013.01)

(58) Field of Classification Search
CPC .......... A61B 2576/023; A61B 5/04011; A61B 5/0071; G16H 30/40; G16H 50/50
See application file for complete search history.

(56) References Cited

U.S. PATENT DOCUMENTS

| | | | |
|---|---|---|---|
| 2007/0049824 A1 | 3/2007 | Konofagou et al. | |
| 2009/0219301 A1 | 9/2009 | Gerard et al. | |
| 2011/0208038 A1* | 8/2011 | Konofagou | A61B 5/055 600/410 |
| 2012/0150024 A1* | 6/2012 | Amit | A61B 1/00082 600/424 |
| 2012/0243758 A1* | 9/2012 | Otani | A61B 8/0883 382/131 |
| 2013/0197881 A1* | 8/2013 | Mansi | A61N 1/3627 703/2 |
| 2013/0211256 A1 | 8/2013 | Russell et al. | |
| 2014/0052118 A1 | 2/2014 | Laske et al. | |
| 2014/0135625 A1* | 5/2014 | Konofagou | A61B 8/0883 600/443 |
| 2014/0148677 A1* | 5/2014 | Liempde | A61B 5/0402 600/389 |
| 2014/0200429 A1 | 7/2014 | Spector et al. | |
| 2014/0276152 A1 | 9/2014 | Narayan et al. | |
| 2015/0057522 A1* | 2/2015 | Nguyen | A61B 5/046 600/374 |
| 2016/0007852 A1* | 1/2016 | Warner | A61B 5/0035 600/374 |
| 2016/0073913 A1* | 3/2016 | Francis | A61B 5/6858 600/374 |
| 2016/0210435 A1* | 7/2016 | Neumann | G16H 50/50 |
| 2017/0049416 A1* | 2/2017 | Azar | A61B 8/08 |
| 2017/0105699 A1* | 4/2017 | Miyaji | A61B 8/5207 |

OTHER PUBLICATIONS

Provost et al., Mapping of Cardiac Electrical Activation with Electromechanical Wave Imaging: An in silico-in vivo Reciprocity Study, Heart Rhythm. May 2011; 8(5): 752-759 (Year: 2011).*

Gurev et al., "Models of cardiac electromechanics based on individual hearts imaging data: Image-based electromechanical models of the heart", Biomech MOdel Mechanobiol. Jun. 2011; 10(3): 295-306 (Year: 2011).*

International Search Report and Written Opinion in co-pending, related PCT Application No. PCT/EP2015/077001, dated Nov. 3, 2016.

Jan Christoph: "Intramural Visualization of Scroll Waves in the Heart", 2014, XP002754847.

\* cited by examiner

METHOD OF AND APPARATUS FOR CHARACTERIZING SPATIAL-TEMPORAL DYNAMICS OF MEDIA EXCITABLE FOR DEFORMATION

CROSS REFERENCE TO RELATED APPLICATIONS

This application is a continuation of International Application PCT/EP2015/077001 with an International Filing Date of Nov. 18, 2015 and claiming priority to European Patent Application No. 15 150 588.0 entitled "Method of and Apparatus for Characterizing Spatial-Temporal Dynamics of Media Excitable for Deformation", filed on Jan. 9, 2015.

FIELD

The present invention relates to a method of characterizing spatial-temporal dynamics of a medium excitable for deformation. Further, the invention relates to an apparatus for visualizing spatial-temporal dynamics of a medium excitable for deformation. Particularly, the medium excitable for deformation may be a myocardium.

Cardiac arrhythmias such as life-threatening ventricular fibrillation are associated with rapid, highly irregular electrical activity propagating in a wave-like manner through the heart and inducing fibrillatory contractions of the muscle tissue. The fibrillatory cardiac electrical and mechanical activity remains poorly understood as it is prohibitively difficult to measure and visualize throughout the volume of the cardiac muscle.

BACKGROUND

US 2014/0276152 A1 discloses a system and method of identifying a driver of a source associated with a heart rhythm disorder. The driver has the form of persistent rotational or centrifugal patterns associated with sensed cardiac electrical activity of a patient. In connection with determining the source of a heart rhythm disorder, data is assessed from a plurality of sensors representing biological activity of the heart. The sensors detect cardiac electrical information. The sensors may be inserted into the heart of a patient or may detect cardiac electrical information via the patient's surface. US 2014/0276152 A1 states that some sensors may also derive electrical cardiac information from cardiac motion of a non-electrical sensing device, e.g. echocardiogram. US 2014/0276152 A1, however, gives no details with regard to using such sensors. Further information is only given for sensors positioned at respective sensor locations adjacent to or contacting tissue in the heart or near the heart under consideration. The detected cardiac electrical information is forwarded to a signal processing device configured to process the information to identify rotational electrical activity or centrifugal activity. Additionally, the computing device identifies indices of driver activity that are persistent. The computing device displays an activation propagation map video that combines and spatially lays out data from a plurality of monophasic action potential voltage representations of the cardiac signals. An arrow indicates rotational movement of displayed information. The rotational activation is indicated from phase mapping by a phase singularity. In the video, the phase singularity may be displayed as a white dot.

US 2014/0052118 A1 discloses a method and system capable of identifying ectopic foci, rotors, or conduction pathways involved in reentrant arrhythmias within cardiac tissue. The system includes a medical device having one or more mapping elements and a computer programmable to identify ectopic foci and rotors within the cardiac tissue based at least in part on signals derived from the plurality of mapping elements at one or more tissue locations. The mapping elements are sensors or electrodes capable of sensing electrical activity within the myocardial cells as the cells polarize and depolarize, such as monophasic action potential electrodes.

US 2014/0200429 A1 discloses methods and systems for mapping cardiac fibrillation in a patient. The methods include deploying a catheter in the patients heart. The catheter includes an array of at least one stacked electrode pair having a first electrode and a second electrode. Each electrode pair is configured to be orthogonal to the surface of the cardiac tissue substrate. A plurality of measurements are obtained from the electrode array in response to electrical activity in the cardiac tissue substrate for a duration indicative of a number of electric circuit cores and distribution of the electric circuit cores across the cardiac tissue substrate in the patients heart. The measurements are processed to obtain the density and distribution of electrical circuit cores which are mapped onto a representation of the patient's heart.

WO 2013/123549 A1 discloses a method for identifying a cardiac region for ablation to prevent or treat a cardiac arrhythmia. The method comprises determining one or more electrical waveform characteristics at a plurality of cardiac sites, identifying a cardiac region of maximal variance of the one or more electrical waveform characteristics, and identifying the cardiac region of maximal variance as the cardiac region for ablation. Determining of the electrical waveform characteristics comprises electrocardiography, particularly bipolar electrocardiography. The identification of the cardiac region of maximal variance comprises generating a map of the electrical waveform characteristics. The identified cardiac region for ablation is a cardiac rotor region, a region of endocardial/epicardial breakthrough, a region of transmural reentry, or a region of discontinuous propagation.

US 2007/0049824 A1 discloses a system and method for detecting electromechanical wave propagation within a body structure of a patient in a series of image frames representing movement of the body structure. Image data comprising a series of image frames corresponding to the movement of the body structure is acquired. A correlation calculation is performed on the image frames to generate a displacement map representing the relative displacement between the first and second image frames. A video is generated comprising a series of displacement maps. The parameters of movement of the body structure are detected by analysis of the displacement maps. The image acquisition may detect the movement of the body structure without inducing such a movement. Particularly, the image data is acquired with an image detection device such as an ultrasound probe, which is used to create images of a heart or other organ or structure of a patient. The known method thus makes use of an elasticity imaging technique which is able to evaluate mechanical wave propagation to provide an estimation of electrical propagation in an noninvasive manner. Based on the discovery that in the context of certain diseased or affected tissue, an electromechanical wave was observed, through sequential images, to travel faster than in normal tissue, the known method provides an imaging method for detecting such conditions, like for example myocardial ischemia.

WO 2014/059170 A1 discloses techniques for mapping behavior of a heart, including cardiac rhythm. A series of images of the heart is taken at one or more pixel locations. Each pixel location corresponds to a region of the heart. Image data corresponding to the pixel locations is obtained, and a periodicity of the image data measured for each of the pixel locations over the series of images is measured. The periodicity corresponds to an electromechanical signal of the heart in the region corresponding to the measured one or more pixel locations. By these techniques, spatial-temporal maps of a heart can be obtained which show the electromechanical patterns of atrial flutter, fibrillation and tachycardia in the heart. During focal arrhythmias such as preventricular contraction and focal atrial tachycardia, electromechanical wave imaging can be used to identify the location of the focal zone and the subsequent propagation of cardiac activation. In the known techniques, electromechanical wave imaging can be integrated in an ultrasound system to characterize the mechanical and electromechanical function representative of atrial and ventricular arrhythmias. Further, intracardiac echocardiography can be used to provide real-time imaging of the heart to identify anatomic structures and guide ablation. Intracardiac echocardiography may also be utilized along with myocardial elastography to asses strains at a high temporal resolution.

U.S. Pat. No. 8,666,138 B2 discloses methods and systems for a functional imaging of cardiac tissue based in the ability of imaging technologies to detect wave-induced tissue deformation at a depth, that allows viewing the propagation of action potentials deep within myocardial tissue. The known methods and systems apply a forward model describing the creation of displacements from known stresses and an inverse model describing the stresses that had to be present to create a given displacement field. In these models, the myocardium is considered to be an elastic, incompressible medium with anisotropy properties that are considered to be known.

US 2009/0219301 A1 discloses an ultrasonic imaging system for evaluating and displaying a deformation of a body organ. A sequence of image data sets comprising at least a first image data set and a second image data set of echographic data is acquired. A motion vector field is calculated between image points of the second image data set and image points of the first image data set. A reference point is chosen within or outside the first and second image data sets. A first scanline is defined, which comprises said reference point. A motion vector of an image point is projected onto the defined first scanline, which provides a projected tissue velocity along the first scanline. The projected tissue velocity is used for evaluating a component of a deformation of the body organ at the image point along the direction of the first scanline. Such a component of a deformation of the body organ, for example a strain rate or a strain, is further rendered in a graphical representation of the sequence of image data sets. In this known imaging system no elastic model of the respective body organ defining elastic interactions between the elements of the body organ is used.

US 2013/0211256 A1 discloses a method for myocardial segment work analysis based on strain and pressure measurements. The method is based on a pressure measurement or estimate and a measurement of strain, preferably by echocardiography, such as speckle tracking ultra sound imaging. An apparatus for receiving, preparing and presenting data related to individual myocardial segment work from tissue strain imaging data comprises a medical imaging device for non-invasively recording tissue strain imaging data for two or more myocardial segments; and an electronic processor capable of calculating mechanical power and/or mechanical work, traces for two or more individual myocardial segments as a function of time for a period comprising the time interval from the beginning of isovolumetric contraction and until the end of isovolumetric relaxation from ventricular tissue strain traces for each of the two or more myocardial segments, and a non-invasively determined pressure trace proportional to a ventricular pressure and in temporal synchrony with the strain traces. In this known method no elastic model of the respective myocardium defining elastic interactions between the elements of the myocardium is used.

It is the object of the present invention to provide a method of characterizing spatial-temporal dynamics of a medium excitable for deformation and an apparatus for visualizing spatial-temporal dynamics of a medium excitable for deformation, which allow for non-invasively imaging mechanical activity of the medium in a way reflecting the temporal development of an electrical activity exciting the medium for deformation.

SUMMARY OF THE INVENTION

The present invention relates to a method of characterizing spatial-temporal dynamics of a medium excitable for deformation. The method comprises defining an elastic model of the medium; imaging the medium at consecutive points in time to obtain a series of images; determining shifts of structures of the medium between the images of the series; adapting a dynamic description of a temporal development of spatial deformations of the elastic model to match the shifts of the structures; and identifying, from the dynamic description, temporal developments of rate of deformation patterns in the medium.

Further, the present invention relates to an apparatus for visualizing spatial-temporal dynamics of a medium excitable for deformation. The apparatus comprises an imaging system configured to image the medium at consecutive points in time to obtain a series of images; an evaluation system configured to determine shifts of structures of the medium between the images of the series; and a visualization system. The evaluation system is configured to identify rate of deformation patterns in the medium by means of: defining an elastic model of the medium; imaging the medium at consecutive points in time to obtain a series of images; determining shifts of structures of the medium between the images of the series; adapting a dynamic description of a temporal development of spatial deformations of the elastic model to match the shifts of the structures; and identifying, from the dynamic description, temporal developments of rate of deformation patterns in the medium. Alternatively, the evaluation system is configured to derive corresponding electrical patterns in the medium. The visualization system is configured to display the rate of deformation or electrical patterns in the medium Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

In the method of characterizing spatial-temporal dynamics of a medium excitable for deformation, the medium is imaged at consecutive points in time to obtain a series of images. Here, the term "image" refers to two-dimensional or three-dimensional image data showing projections, cross-sections or volumes of the medium, or sparsely, arbitrarily sampled representations of the medium. The image data can show the medium either in a regular array along evenly distributed locations in a rasterized fashion or at sparse and arbitrarily distributed locations throughout the medium or in other ways specific to the operational mode of the imaging modality used. Accordingly, the image data can consist of pixels or voxels or any other geometric or volumetric subunits in a structured or unstructured grid organization. Besides a Cartesian coordinate system, the images may be obtained in a polar or spherical coordinate system as in case of 3D echocardiography with sector transducers. The term "image" also covers a set of two-dimensional images, particularly a set of two-dimensional images imaging the medium along a set of parallel imaging planes.

The images of the medium are used to determine shifts of structures of the medium between the images of the series. The structures of the medium whose shifts are determined are any structures recognizable in the images. Correspondingly, the structures of the medium evaluated will depend on the imaging technique applied. A dynamic description of a temporal development of spatial deformations of a pre-defined elastic model of the medium is adapted to the determined shifts of the structures of the medium.

The elastic model may involve a mathematical and computational description of an elastic continuous body undergoing, possibly finite and both affine or non-affine, deformations with continuum mechanical constitutive laws being set or adapted to the specific material properties of the medium. For example, in a discrete description of the medium, the model may consist of a set of particles occupying the space or volume defining the medium and the set of particles may retain specific particle-interactions that introduce elastic or soft-tissue-like behavior and support vibrations and waves throughout the medium as the system of particles seeks a particular stress equilibrium dynamically. Also, the interaction scheme may allow to introduce preferred orientations and other elastic, possibly nonlinear, behavior specific to the medium. Also continuous computational and visco-elastic descriptions may be employed to model the elasticity of the medium, for example. The elastic model may furthermore involve a mathematical and computational description for internal processes occurring within and leading to a deformation of the medium excitable for deformations. For example, the elastic model may consider that a strain wave caused by an electrical action potential wave will not be reflected like a standard elastic wave but also contains components of internal active stress.

The elastic model is predefined to describe the elasticity of the medium. The dynamic description of the temporal development of spatial deformations of the elastic model may also be referred to as a dynamic model of the medium. The dynamic description or model is adapted to match the determined shifts of the structures. From the dynamic description or model, temporal developments of rate of deformation patterns in the medium are identified. Here, rate of deformation generally refers to dynamic continuum mechanical measures of deformation, that is, the rate at which local material elements of the continuum body deform, i.e. strain rates or strain rate accelerations. These kinematic measures may be derived and used in terms of the rate of deformation tensor or strain rate tensor directly or be obtained as the derivatives of the deformation tensor with respect to time for further analysis, for example. Also, tensor-valued measures of deformation and rate of deformation may be reduced to vector-, or scalar-valued measures of deformation or rate of deformation respectively, using invariants or eigenvalue decompositions of the tensors such as principal strains and stretches or similar kinematic quantities and their behavior over time, for example.

The inventors could prove that the method according to the present invention is able to, for example, spatially and temporally resolve mechanical vortex rotor activity occurring in a myocardium affected by ventricular fibrillation. They could also prove that these mechanical vortex rotors are strongly correlated with electrical action potential scroll wave activity involved in ventricular fibrillation. The correlation between the mechanical vortex rotors and the electrical action potential scroll wave rotor is so strong that the method according to the present invention may be used to image electrical action potentials by means of the rate of deformation patterns resulting in the medium. But even without aiming for imaging the electrical activity, imaging the mechanical activity according to the present invention will provide a valuable tool for characterizing the dynamic activity and state of the medium.

Particularly, the method of the present invention allows for identifying centers of rotation from the dynamic description or model. These centers of rotation are those points of the medium around which rate of deformation patterns rotate in the medium. Rotating electrical action potential wave patterns are associated with electrical spiral and scroll wave activity, which is thought to be the pattern-forming, self-organizational mechanism underlying cardiac fibrillation. Spiral and scroll wave rotors form dynamically around centers of rotation, which can be depicted by phase singular points in two and lines of phase singularity in three dimensions respectively. The rotating electrical activity interacts with the heterogeneous cardiac substrate. Specifically, the rotational core regions of scroll waves are thought to anchor to anatomic obstacles or heterogeneities within the myocardium. In the same time, the obstacles and heterogeneities themselves can be activated as sources of electrical activity and can be employed for the control and termination of fibrillation using low-energy anti-fibrillation pacing techniques. Consequently, the development of therapeutical strategies for the successful termination or control of cardiac fibrillation relies on a thorough knowledge about the organization of the underlying electrical pattern, for example and more specifically, the positions and alignments of the rotational core regions of rotational structures of the turbulent electrical wave pattern within the myocardium. Thus, identifying the centers of rotation according to the present invention is of a particular value as the inventors showed that these centers of rotation identified from the dynamical description or model coincide with the centers of rotation of the respective action potential causing the deformation of the medium, e.g. the myocardium.

However, the method of the present invention is not limited to the identification of rotational centers. It may also be used to identify other activity patterns such as, for instance, focal or centrifugal activity patterns. For this purpose, the rate of deformation patterns identified from the dynamic description or model may be transformed into electrical activity (i.e. action potential, calcium transient) patterns using a further electrical model of the respective medium, that is coupled to the elastic model in such a way that both models together constitute an electro-mechanical model. Alternatively, the elastic model may also cover the special electro-mechanical properties of the medium, i.e. the correlation between electrical action potential or calcium transient and mechanical deformation of the medium, including any inhomogeneity of this correlation.

The incorporation of an electrical model into the method according to the present invention may enhance the imaging procedure as the electrical model may provide constraints to possible solutions of the adaptation of the elastic model to the measured deformations of the imaged tissue body. These constraints correspond to imposing dynamic boundary conditions or a time-order or -dependence onto the adaptation procedure of the elastic model. In the heart, for instance, the particular behavior of the electrical activity, such as the directionality of wave propagation that produces characteristic wave phenomena as well as the annihilation of waves at the medium boundaries, causes particular deformations of the muscle and these deformations could be enforced to occur in the development of the adapting elastic model rather than other, unphysical or untypical types of deformations and their according temporal developments. In particular, the electrical model together with a mechanism that initiates electrical activity in this electrical model according to a certain rule and based on events measured or observed in the elastic model then may produce electrical wave patterns that evolve separately from but accordingly to the elastic activity. As the electrical activity in the electrical model could due to the coupling also initiate contractile forces or deformations in the elastic model, it could influence the adaptation of the elastic model to the deformations of a measured tissue body and it could do so in an iterative procedure, for instance. As an example, dynamic events occurring in the elastic model could cause the corresponding elements or parts in the electrical model to become excited and trigger the propagation of waves of electrical activity in the electrical model. These wave patterns of electrical activity could be visualized as such or they could be used to, for instance, trigger contraction or deformations of the corresponding elements or parts in the elastic model. As a result, the adaptation of the elastic model to the deformations of a measured tissue body would include active internal stress components leading to a deformation. Also, other coupling mechanisms may be implemented in the coupling between electrical and elastic model depending on the coupling desired. For instance, the electrical model could comprise mechanisms that induce electrical excitation whenever corresponding elements or parts of the elastic model experience mechanical stretch.

In one embodiment of the method according to the present invention, rate of deformation patterns identified from the dynamic description or model are displayed as phase portraits or phase representations. In such a phase portrait, the positions of the mechanical wave fronts are depicted at different phases by different colors, for example. The shape of the wave fronts and their course through the medium may be taken from these phase portraits. Thus, the phase portraits allow for seeing which parts of the medium are affected by which topological activity pattern and by which mechanical rotor, for example. Any centers of rotation may be displayed as phase singular points or lines of phase singularity in the phase portraits. Likewise, computed electrical patterns derived from the electrical model may be displayed as phase portraits or phase representations.

The imaging techniques used in the method of the present invention for imaging the medium at consecutive points in time may, for example, be ultrasound imaging, particularly two- or three-dimensional brightness-mode ultrasound imaging, magnetic resonance imaging but also optical imaging techniques such as optical coherence tomography, light sheet imaging or microscopy. The structures of the medium depicted by ultrasound imaging will include structures defined by elastic and acoustic reflective properties of the medium. As the elasticity of a deformable medium is affected by the strain of the medium, the structures depicted include direct information on the strain and strain rate distribution in the medium.

The shifts of the structures of the medium may actually be determined using correlation-based speckle tracking techniques or other image registration and motion tracking techniques. These techniques are well known as such and may be executed automatically and quickly to execute the entire method according to the present invention at real time or close to real time. Also other information directly available from the imaging modality about possible shifts of the medium may be used.

The choice of parameters of the elastic and electrical models involved may be made appropriately before or during the imaging procedure as the parameters may be identified during imaging from the dynamic behavior of the data driven analysis modeling. In addition, parameters may be set based on the behavior of ab electrocardiogram, which is likely available at any time during the imaging procedure.

In the method according to the present invention, the elastic model of the medium and the dynamic description of the temporal development of the spatial deformations of the elastic model fill the gaps between the speckles or structures tracked. Even with a low level of detail of the definition of the elastic model and a low level of adaptation of the elastic model to the actual medium, the elastic model and the dynamic description of the temporal development of its spatial deformations allow for monitoring the strain rate patterns of interest. Nevertheless, an adaptation of the elastic model to the actual elastic properties of the medium based on the dynamic description enhances the accuracy, i.e. the spatial and temporal resolution in imaging the rate of deformation patterns in the medium. If, for example, the propagation of a mechanical wave front in the medium is much quicker in one direction than in another direction, or the rate of deformation pattern expresses strong spatial gradients or other dynamic features or particular behavior along preferred orientations, this may indicate that the medium is not isotropic but has a fibrous structure with fibers extending along the direction of the fastest propagation. In this way, the direction of muscle fibers of a myocardium may be determined and implemented in the elastic model of the myocardium, for example. Next to anisotropy, contractile and elastic heterogeneity may be assessed and incorporated into the model. Also, if, for example, the rate of deformation was measured using the dynamic description or model and the information was found to provide an estimate of the distribution of the underlying processes within the medium responsible for the deformation, such as for instance electrical excitation or contractile activity, an adaptation of the dynamic model to include this information may serve to enhance the accuracy of the model. Such an estimate may be obtained by analyzing dynamic features of the spatial temporal evolution of the model, for example. Such an estimate may also be obtained using modeling of the internal processes as stated above and synchronizing or converging the two parts of the model in an iterative and dynamic procedure.

As already indicated above, centers of rotation or focal activity identified from the dynamic description or model may be targeted in a therapy directed against the formation of spiral or scroll wave rotors like they are occurring during ventricular fibrillation or against other reentrant and arrhythmic cardiac activity. More particularly, one or more of the centers of rotation or the centers of focal activity may be selected as a set of reference points to identify suitable ablation targets based on the method according to the present invention. Also, possibly abnormal, heterogeneous contractile activity or elastic behavior that can be identified using the dynamic description or model may be linked to fibrotic structures and be used to identify locations for ablation or other forms of treatment. Further, an ablation instrument used for ablating these ablation targets may be guided by means of the same imaging technique used for imaging the medium.

Also, one or more of the centers of rotation or the centers of focal activity may be selected as a set of reference points to identify suitable pacing targets based on the method according to the present invention. Further, a pacing instrument used for pacing these pacing targets may be guided by means of the same imaging technique used for imaging the medium. One or more of the centers of rotation or the centers of focal activity may be used to visualize and analyze the topological structure of the cardiac activity. That is, in two spatial dimensions, as for instance in the case of an extended, thin medium excitable for deformations, the topological structure may be depicted by the behavior of the number, density distribution, creation and annihilation rates and motility of phase singular points and their surrounding time-varying phase portrait map of the activity. In three spatial dimensions, as for instance in the case of a bulk medium excitable for deformations, the topological structure may be depicted by the behavior of the number, alignment, length, density and creation and annihilation rates of lines of phase singularity and their surrounding time-varying phase portrait of the activity. In particular, dynamic features and statistic properties of the dynamics and topological structure of the activity, for example, frequency distributions or the degree of synchronicity of periodic activity, may serve to characterize and distinguish different pathophysiological stages and forms of the activity. For instance, it may serve to characterize and distinguish atrial flutter or tachycardia or different variants of atrial or ventricular fibrillation, or to locate sources of arrhythmic activity or other pivotal areas within the medium contributing to a certain disease state. Knowledge about the organizational, i.e. topological, structure of the activity may serve to develop long-term interventional strategies for the cure or prevention of arrhythmias but also for the development of techniques for immediate intervention of arrhythmic activity and could be used for treatment planning, targeting and evaluation but also for screening pharmaceutical drugs including pharmaceutical, compounds, compositions and other products in vitro.

As an example, in combination with pacing techniques employing, for instance, electrical or optical stimuli or ultrasound-related stimuli below ablative energies, the above described visualization and analysis of the activity could be used to enable interacting with the activity during the imaging procedure by applying accordingly timed stimuli at locations that were specifically chosen based on the information provided by the analysis imaging, to change the inherent structural organization of the activity. The interaction could drive the activity away from long-term pathophysiological states in a therapeutical setting or terminate unstable, arrhythmic activity in an emergency situation.

As another example, in the case that ablation procedures are or were applied, the effectiveness of the application could be monitored or controlled and evaluated during and after the procedure. A change of the activity may be observed and assessed, during and after the procedure, either locally within the ablated areas or globally within larger portions of the medium or the entire medium, given that the ablation can be observed to affect the global activity pattern via the imaging procedure. Further, the steps of imaging the medium, determining shifts of the structures, adapting the dynamic description and identifying temporal developments of the rate of deformation patterns may be carried out prior to, and during and/or after applying a drug to be tested to the medium; and these steps may be repeated for each of a plurality of drugs. The temporal developments of the rate of deformation patterns identified for each of the plurality of drugs may then be compared to each other to select a potential anti-arrhythmic drug from the plurality of drugs. These embodiments of the method of the present invention may be carried out in vivo at a myocardium of a living individual or in vitro at a test medium which also may be a myocardium.

The apparatus according to the present invention for visualizing spatial-temporal dynamics of a medium excitable for deformation comprises an imaging system configured to image the medium at consecutive points in time to obtain a series of images. Particularly, the imaging system may be an ultrasound imaging system. The apparatus further comprises an evaluation system configured to implement the method of the present invention for identifying rate of deformation patterns in the medium; and a visualization system configured to display the rate of deformation patterns in the medium. The visualization system may, for example, display phase portraits of the rate of deformation patterns as well as topological defects such as phase singular points and lines of phase singularity.

The apparatus according to the present invention may further comprise an ablation instrument, particularly an ablation instrument configured to be guided by the imaging system. The ablation instrument may, for example, include a catheter or be a non-catheter based instrument for directing ablational energy to an ablation target. The ablation instrument may further, for example, be based on high-intensity focused ultrasound and be incorporated in the same or be used in combination with the ultrasound device used for imaging the ablation procedure. The ablational energy may, for example, be electric, RF- or light energy or ultrasound-related acoustic energy.

The apparatus according to the present invention may further comprise a pacing instrument, particularly a pacing instrument configured to be guided by the imaging system. The pacing instrument may apply stimuli to the medium at various spatial locations in a well-defined, timed manner based on the information provided by the imaging system. Stimuli may be provided by, for example, electrodes or optical probes providing electrical or optical stimuli respectively. Stimuli may also consist of ultrasound-based acoustic stimuli using focused ultrasound below ablative energies.

Figure 1:
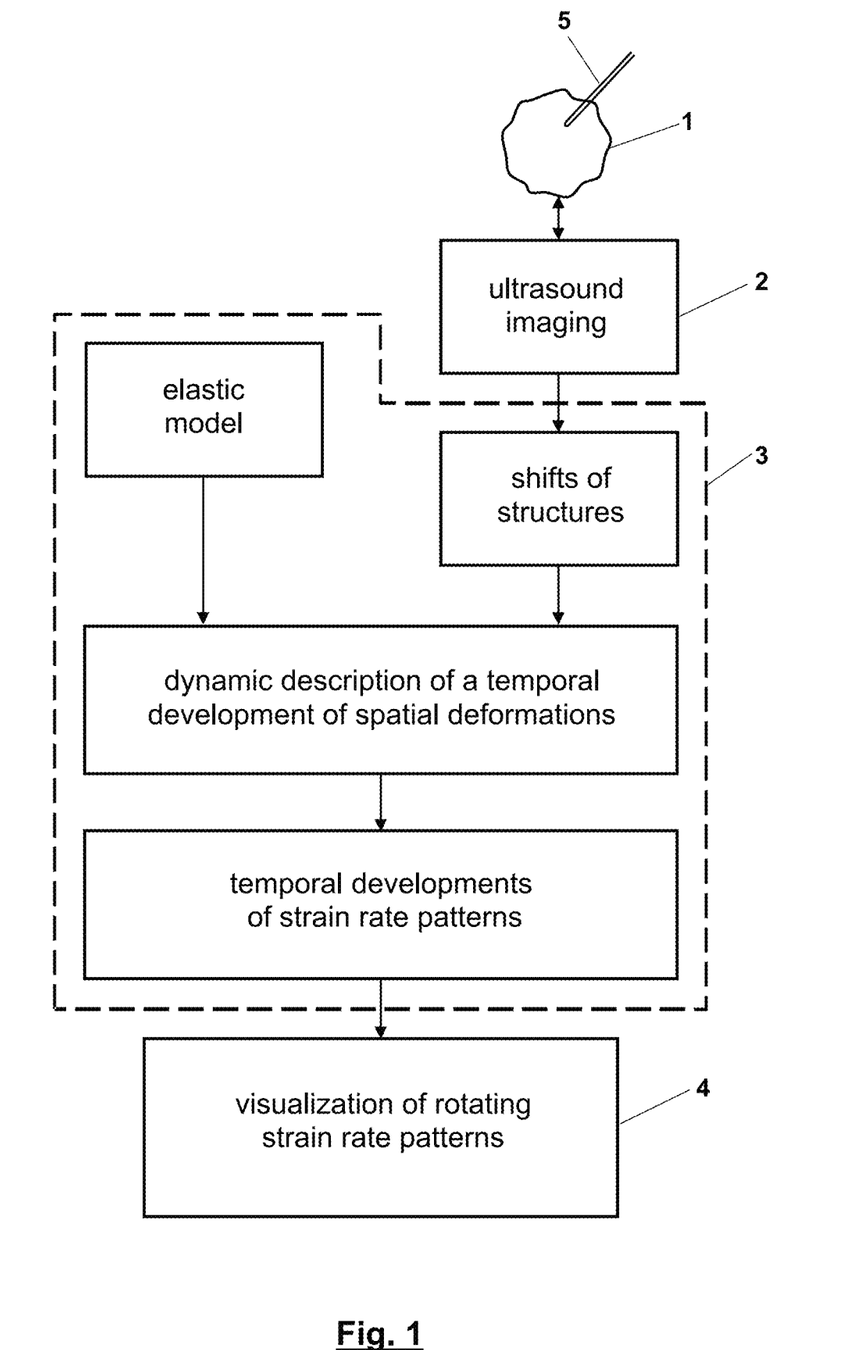
FIG. 1 is block diagram of an embodiment of the method and apparatus of the present invention.

Referring now in greater detail to the drawings, FIG. 1 depicts the various steps of an embodiment of the method of characterizing spatial-temporal dynamics of a medium excitable for deformation according to the present invention. At the same time, FIG. 1 depicts the basic components of an apparatus for visualizing spatial-temporal dynamics of a medium excitable for deformation according to the present invention. The medium 1 excitable for deformation is imaged by an ultrasound imaging device 2 to obtain a series of images of the medium 1. In an evaluation system 3 the images are analyzed for shifts of structures of the medium between the various images. This analysis is based on a correlation-based speckle tracking method, i.e. correlations between consecutive images are evaluated for the shifts of the speckles as indicators of shifts of structures of the medium associated with the speckles. The shifts determined are used to adapt a dynamic description of a temporal development of spatial deformations of a predefined elastic model. The adaptation is made until the dynamic description of the temporal development of spatial deformations of the elastic model of the medium describe the shifts of the structures which have been determined. The dynamic description of the temporal development of the spatial deformations of the elastic model may also be referred to as a dynamic model of the medium 1. From this dynamic model, temporal developments of strain rate patterns in the medium 1 are identified. These strain rate patterns reflect the distribution and temporal development of mechanical activity in the medium 1.

The visualization system 4 which may, for example, be a monitor is used to visualize the identified strain rate patterns, particularly rotating strain rate patterns, together with their centers of rotation. The visualization system 4 may also be used to guide an ablation instrument 5 used for partially ablating the medium 1 and/or a pacing instrument used for applying stimuli at locations within the medium 1 based on the information about the locations of at least one or more centers of rotation visualized. By means of ablating or pacing the medium 1, the cause for a rotating strain rate pattern may be removed. This technique may, for example, be used to remove the cause of ventricular fibrillation of a myocardium. This is possible because the mechanical activity visualized according to FIG. 1 strongly correlates with an electrical action potential in a myocardium.

Figure 2:
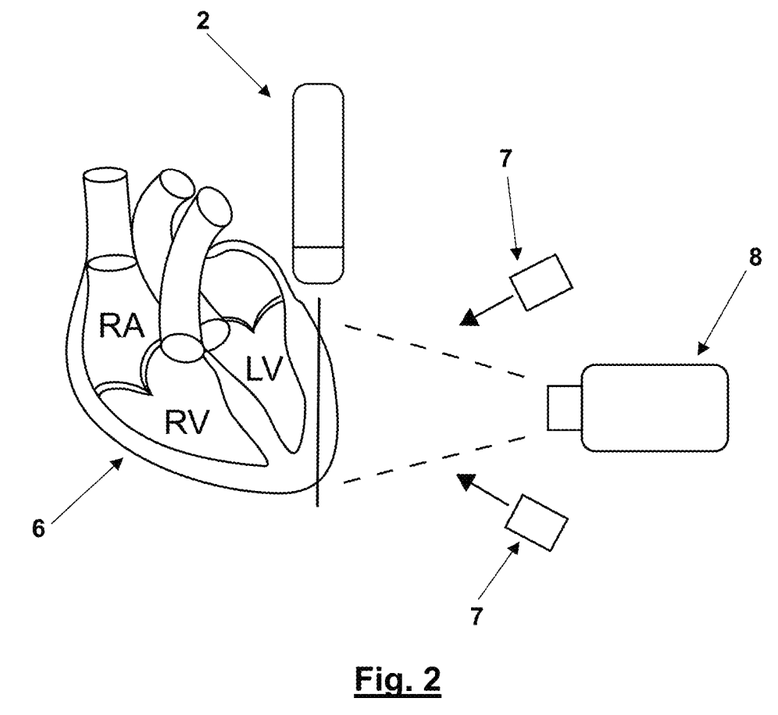
FIG. 2 illustrates a setup for applying one embodiment of the present invention.

FIG. 2 depicts a setup which has been used to show the correlation between mechanical activity and electrical action potential activity on the epicardial surface and within the left ventricular wall of a Langendorff-perfused rabbit heart 6 during ventricular fibrillation. In the heart 6, LV indicates the left ventricle, RV indicates the right ventricle, and RA indicates the right atrium. According to FIG. 1, the mechanical activity was monitored using an ultrasonic imaging device 2 operating in B-mode and providing images at 300 frames per second. The electrical action potential was monitored by fluorescence imaging using a fluorescent probe sensitive to the transmembrane potential and Ca2+ concentration at the surface of the heart 6. The fluorescent probe was excited by fluorescent light from light sources 7, and the fluorescent light was registered with a camera 8 at 500 frames per second.

Figure 3A:
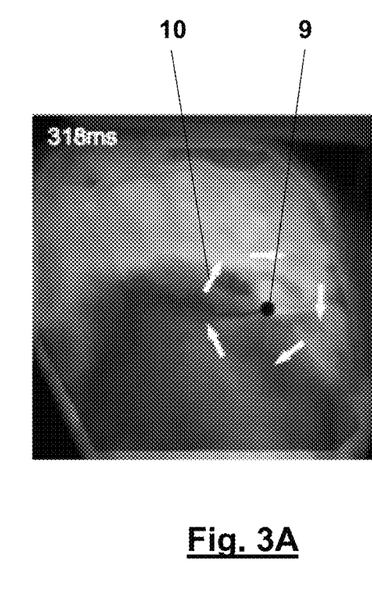
FIG. 3A-FIG. 3B compare an electrical action potential (FIG. 3A) and a mechanical activity (FIG. 3B) both determined with the experimental setup according to FIG. 2.
Figure 3B:
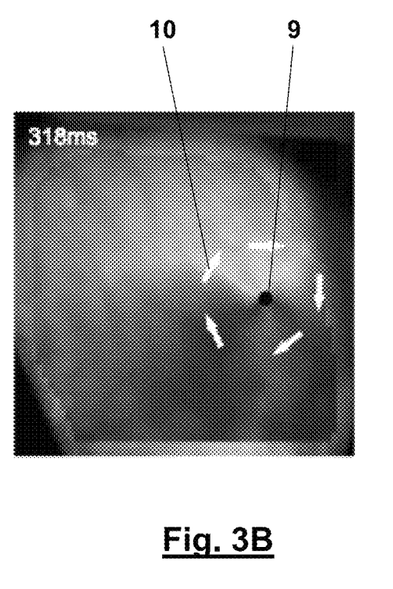

FIG. 3A shows a phase portrait of the electrical actions potential on the surface of the heart 6 according to FIG. 2 in case of an electrical scroll wave rotating about a center of rotation 9 as indicated by arrows 10. FIG. 3B depicts the resulting mechanical scroll wave, i.e. a phase portrait of the strain rate pattern at the same surface as in FIG. 3A rotating about the same center of rotation 9 with a very similar shape of the wave fronts. The direction of rotation also indicated by arrows 10 is the same one as in FIG. 3A, i.e. clockwise, and the frequency of rotation is also the same. Consequently, the center of rotation 9 of the mechanical scroll wave according to FIG. 3B identified by the ultrasound imaging device 2 according to FIG. 2 points to the center of rotation 9 of the electrical scroll wave according to FIG. 3A. Thus, the non-invasive ultrasound imaging device 2 may be used to identify potential ablation targets in a therapy of the ventricular fibrillation displaying the electrical scroll waves according to FIG. 3A.

Figure 4:
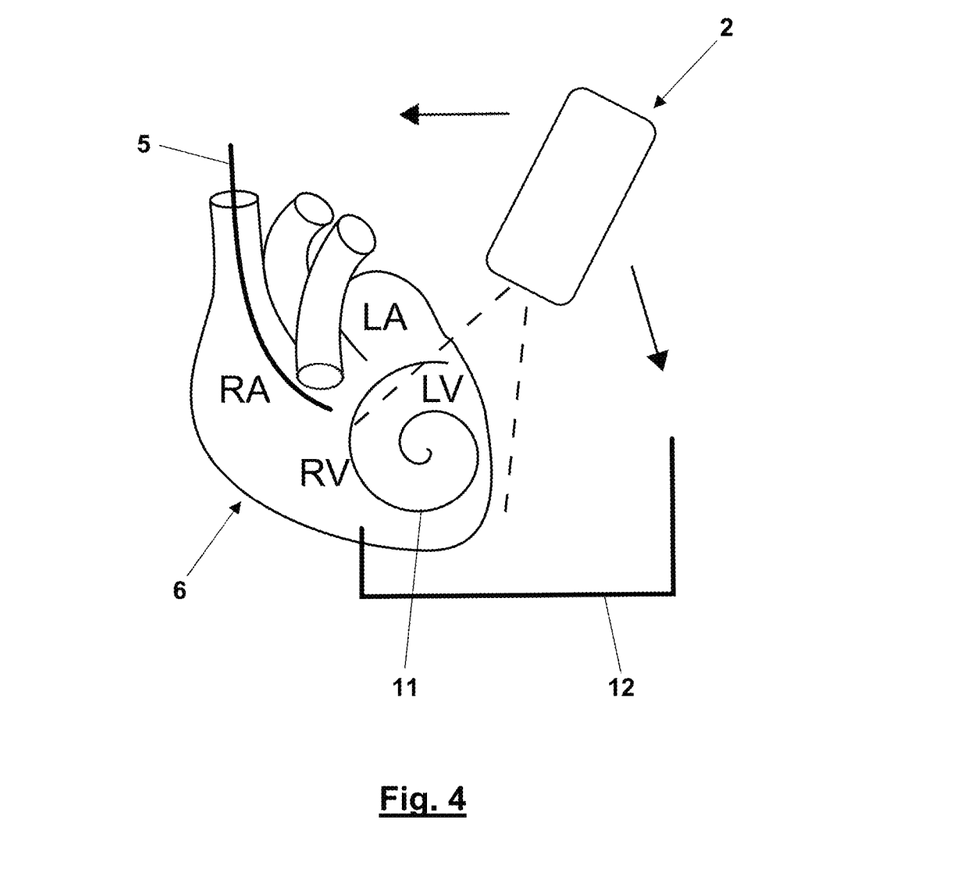
FIG. 4. illustrates another setup for applying another embodiment of the present invention.

FIG. 4 depicts another setup implementing an embodiment of the present invention with a heart 6. The heart 6 may be the heart of a living individual or an in-vitro heart preparation. The mechanical activity of the myocardium of the heart 6 is monitored using an ultrasonic imaging device 2 providing three-dimensional images of the heart 6. These three-dimensional images allows for spatially resolving the mechanical activity in all three spatial dimensions. In FIG. 4, a scroll wave 11 propagating in the myocardium of the heart 6 is indicated. Further, in addition to the indicators in FIG. 2, LA indicates the position of the left atrium of the heart 6. FIG. 4 also shows that the pictures taken with the ultrasonic imaging device 2 may be used for guiding the ablation instrument 5 within the heart and/or a pacing instrument 12 with regard to the heart. By a means of simultaneously monitoring the mechanical activity of the myocardium using the ultrasonic imaging device 2, the effect of any ablation by means of the ablation instrument 5 and/or any pacing by means of the pacing instrument 12 will be seen and may be evaluated in real-time.

Figure 5A:
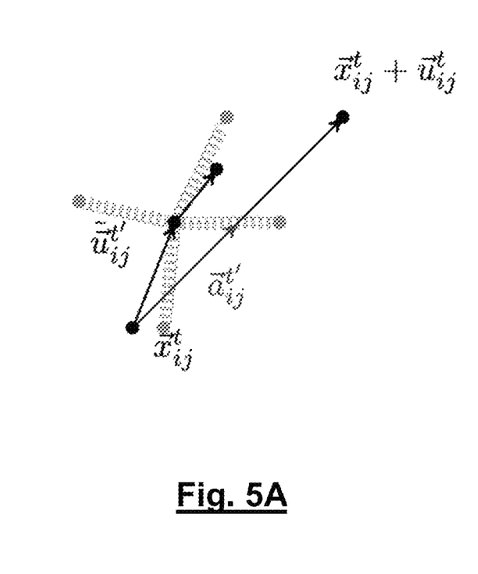
FIG. 5A-FIG. 5C illustrate a possible scheme for adapting an elastic model to track deformation dynamically, including acceleration of an element of the respective medium (FIG. 5A), iterative adaptation of the dynamic description of the elastic model (FIG. 5B) and final solution of the adaptation of the dynamic description of the elastic model (FIG. 5C); and FIG. 6A

FIG. 5A depicts how an element of the respective medium is accelerated along an acceleration vector a towards a supposed tracked position of the medium element $x(t+1)=x(t)+u(t)$ in a next time step. Passive elastic forces of the elastic model of the medium acting on the medium element x indicated by springs result in a shift u deviating from a straight shift in the direction of vector a.

Figure 5B:
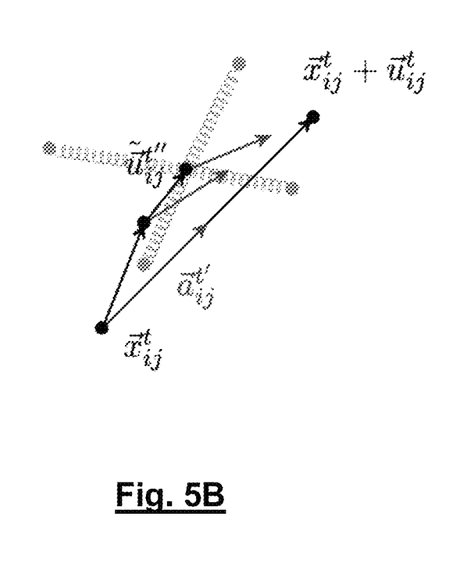

FIG. 5B illustrates the iterative adaptation of the dynamic description of the elastic model to the tracked displacement field using successive accelerations of the medium particles and equilibration of the configuration of the medium elements. An individual medium element moves along a trajectory given by u.

Figure 5C:
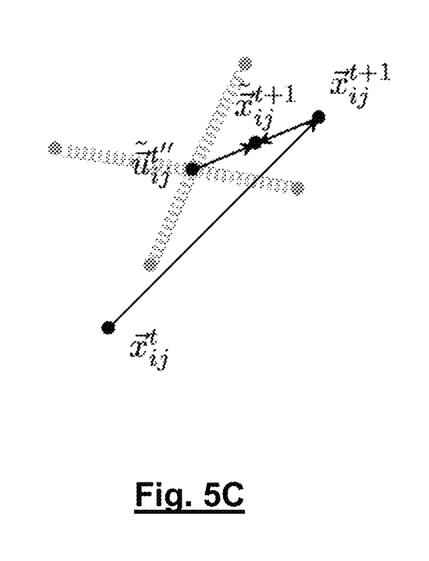

FIG. 5C illustrates a possible final solution of the adaptation of the dynamic description of the elastic model based on an approximation of the raw shift. The final position of the medium element is a spatial average of the raw shift and the final position of the particle in the elastic model.

Figure 6A:
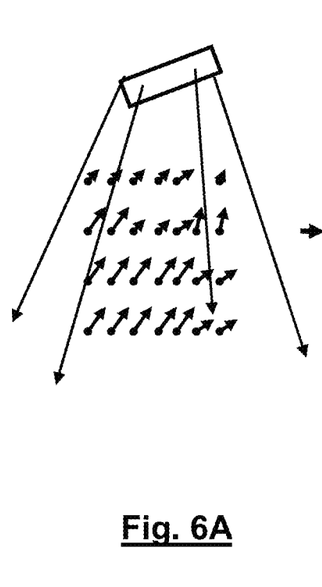

FIG. 6A illustrates determination of shifts of structures of the respective medium between two images of the medium.

Figure 6B:
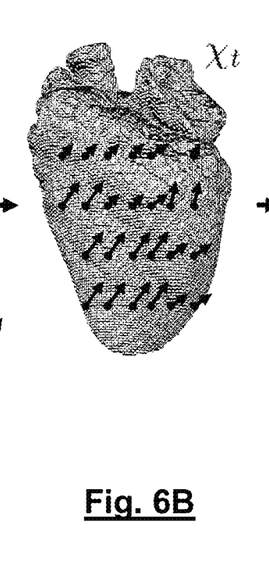

FIG. 6B depicts adapting a dynamic description of a temporal development of spatial deformations of an elastic model of the medium to match the shifts of the structure.

Figure 6C:
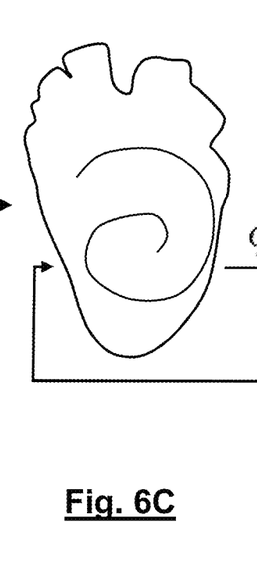

FIG. 6C depicts identifying, from the dynamic description, temporal developments of the rate of deformation patterns in the medium illustrated as a mechanical scroll wave.

Figure 6D:
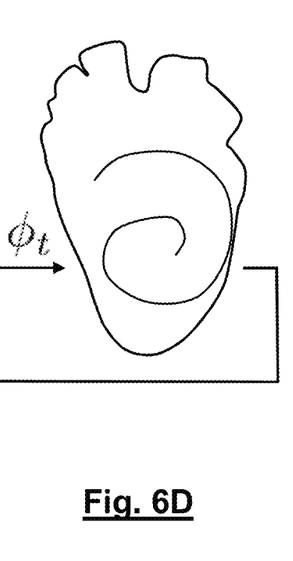
-FIG. 6D illustrates the steps of the method according to the present invention including a step of determining shifts of structures of the respective medium (FIG. 6A), adapting a dynamic description of a temporal development of special deformation of an elastic model (FIG. 6B), identifying temporal developments of the rate of deformation patterns in the medium (FIG. 6C) and a final step of transforming a rate of deformation pattern into an electrical action potential pattern using an electro-mechanical model of the respective medium (FIG. 6D).

FIG. 6D illustrates transforming the rate of deformation pattern into an electrical action potential pattern which is illustrated as an electrical scroll wave using a further electro-mechanical model of the medium. Additionally, in FIGS. 6C and 6D, an iterative adaptation of the electro-mechanical model and the elastic model is indicated.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of characterizing spatial-temporal dynamics of a medium excitable for deformation, the method comprising:
   defining an elastic model of the medium;
   defining a dynamic model of the medium that provides a description of a temporal development of spatial deformations of the elastic model;
   imaging the medium at consecutive points in time to obtain a series of images;
   determining shifts of structures of the medium between the images of the series;
   adapting the dynamic model to match the shifts of the structures of the medium;
   identifying, from the dynamic model, temporal developments of rate of deformation patterns in the medium,
   wherein centers of rotation, around which the rate of deformation patterns rotate with mechanical vortex rotor activity occurring in the medium, are identified from the dynamic model,
   further comprising
   mapping electrical activity of the medium by means of the rate of deformation patterns, wherein the rate of deformation patterns are transformed into patterns of electrical activity by:
   defining an electrical model of the medium;
   coupling the elastic model of the medium to the electrical model of the medium; and
   adapting a temporal development of the electrical activity of the electrical model of the medium to the temporal developments of the rate of deformation patterns in the coupled elastic model of the medium.

2. The method of claim 1, wherein centers of electrical rotation, around which the patterns of electrical activity rotate in the medium, are identified from the temporal development of the electrical activity.

3. The method of claim 1, wherein the patterns of electrical activity in the medium are displayed as phase portraits.

4. The method of claim 1, wherein the rate of deformation patterns in the medium are displayed as phase portraits.

5. The method of claim 4, wherein the centers of rotation are displayed as phase singular points or lines of phase singularity in the phase portraits.

6. The method of claim 1, wherein the medium is imaged by at least one of
   ultrasound imaging,
   magnetic resonance imaging,
   optical coherence tomography,
   optical imaging and
   microscopy.

7. The method of claim 1, wherein the shifts of the structures of the medium are determined using at least one of
   image registration,
   motion tracking,
   spatial correlation and
   correlation-based speckle tracking.

8. The method of claim 1, wherein the elastic model is adapted to actual elastic properties of the medium based on the adapted dynamic model.

9. The method of claim 1, wherein the medium is a myocardium.

10. The method of claim 1, wherein at least one of the centers of rotation is selected as a reference point for the identification of an ablation or pacing target.

11. The method of claim 1, wherein at least one of an ablation instrument and a pacing stimuli instrument is guided by means of the step of imaging the medium.

12. The method of claim 1, wherein the steps of imaging the medium, determining shifts of the structures of the medium, adapting the dynamic model and identifying temporal developments of the rate of deformation patterns are executed prior to, and at least during or after applying a drug to be tested to the medium.

13. The method of claim 12,
   wherein executing the steps of imaging the medium, determining shifts of the structures of the medium, adapting the dynamic model and identifying temporal developments of the rate of deformation patterns prior to, and at least during or after applying a drug to be tested to the medium is repeated for each of a plurality of drugs, and
   wherein the temporal developments of the rate of deformation patterns identified for each of the plurality of drugs are compared to each other to select a potential anti-arrhythmic drug from the plurality of drugs.

14. The method of claim 1, wherein the method is carried out at the medium kept in vitro.

15. An apparatus for visualizing spatial-temporal dynamics of a medium excitable for deformation, the apparatus comprising:
   an imaging system configured to image the medium at consecutive points in time to obtain a series of images;
   an evaluation system configured to determine shifts of structures of the medium between the images of the series; and
   a visualization system;
   wherein the evaluation system is configured
      to map electrical activity of the medium by means of:
         defining an elastic model of the medium;
         defining a dynamic model of the medium that provides a description of a temporal development of spatial deformations of the elastic model;
         defining an electrical model of the medium; and
         adapting the dynamic model to match the shifts of the structures;
         identifying, from the dynamic model, temporal developments of rate of deformation patterns in the medium; and transforming the rate of deformation patterns into electrical action potential wave patterns associated with electrical spiral and scroll wave activity by:
coupling the elastic model of the medium to the electrical model of the medium; and
adapting a temporal development of the electrical activity of the electrical model of the medium to the temporal developments of the rate of deformation patterns in the coupled elastic model of the medium; and
identifying centers of rotation, around which the electrical action potential wave patterns rotate in the medium, from the temporal development of electrical activity and
wherein the visualization system is configured to display the rate of deformation or electrical action potential wave patterns in the medium.

16. The apparatus of claim 15, wherein the imaging system includes at least one of
an ultrasound imaging device,
a magnetic resonance imaging device,
an optical coherence tomography device,
a camera and
an optical microscope.

17. The apparatus of claim 15, further comprising at least one of an ablation instrument and a pacing stimuli instrument configured to be guided by the imaging system.

18. A method of characterizing spatial-temporal dynamics of a medium excitable for deformation, the method comprising:
defining an elastic model of the medium
defining a dynamic model of the medium that provides a description of a temporal development of spatial deformations of the elastic model;
defining an electrical model of the medium;
imaging the medium at consecutive points in time to obtain a series of images;
determining shifts of structures of the medium between the images of the series;
adapting the dynamic model to match the shifts of the structures of the medium;
identifying, from the dynamic model, temporal developments of rate of deformation patterns in the medium; and
mapping electrical activity of the medium by means of the rate of deformation patterns; wherein the rate of deformation patterns are transformed into electrical action potential wave patterns associated with electrical spiral and scroll wave activity by:
coupling the elastic model of the medium to the electrical model of the medium; and
adapting a temporal development of the electrical activity of the electrical model of the medium to the temporal developments of the rate of deformation patterns in the coupled elastic model of the medium; and
identifying centers of rotation, around which the electrical action potential wave patterns rotate in the medium, from the temporal development of the electrical activity.

19. The method of claim 18, wherein the electrical action potential wave patterns in the medium are displayed as phase portraits.

* * * * *